(12) United States Patent
Miller et al.

(10) Patent No.: US 9,302,012 B2
(45) Date of Patent: Apr. 5, 2016

(54) ANTI-BACTERIAL SIDEROPHORE-AMINOPENICILLIN CONJUGATES

(71) Applicant: University of Notre Dame Du Lac, Notre Dame, IN (US)

(72) Inventors: Marvin J. Miller, South Bend, IN (US); Cheng Ji, New York, NY (US); Patricia A. Miller, South Bend, IN (US)

(73) Assignee: UNIVERSITY OF NOTRE DAME DU LAC, Notre Dame, IN (US)

( * ) Notice: Subject to any disclaimer, the term of this patent is extended or adjusted under 35 U.S.C. 154(b) by 171 days.

(21) Appl. No.: 13/865,801

(22) Filed: Apr. 18, 2013

(65) Prior Publication Data

US 2013/0281424 A1 Oct. 24, 2013

Related U.S. Application Data

(60) Provisional application No. 61/687,101, filed on Apr. 18, 2012.

(51) Int. Cl.
| | | |
|---|---|---|
| *A61K 31/167* | (2006.01) | |
| *A61K 31/235* | (2006.01) | |
| *A61K 47/48* | (2006.01) | |

(52) U.S. Cl.
CPC ......... *A61K 47/48023* (2013.01); *A61K 31/167* (2013.01); *A61K 31/235* (2013.01); *A61K 47/48076* (2013.01)

(58) Field of Classification Search
CPC ........................... A61K 31/167; A61K 31/235
See application file for complete search history.

(56) References Cited

U.S. PATENT DOCUMENTS

2004/0132707 A1 7/2004 Heinisch

OTHER PUBLICATIONS

Heinisch et al., Highly Antibacterial Active Aminoacyl Penicillin Conjugates with Acylated Bis-Catecholate Siderophores Based on Secondary Diamino Acids and Related Compounds, J. Med. Chem. (2002) 45: 3032-3040.
Heinisch et al., "Synthesis and Biological Activity of Tris-and Tetrakiscatecholate Siderophores Based on Poly-aza Alkanoic Acids or Alkylbenzoic Acids and their Conjugates with β-Lactam Antibiotics," Arzneim-Forschung/Drus Res. (2003) 53 (3): 188-195.
Ji et al., "Exploiting bacterial iron acquisition: siderophore conjugates," Future Med. Chem. (2012) 4 (3): 297-313.
Möllmann et al., "Siderophores as drug delivery agents: application of the "Trojan Horse" strategy," Biometals (Feb. 12, 2009) 22: 615-624.
Raymond et al., Enterobactin: An archetype for microbial iron transport, PNAS (Apr. 1, 2003) 100 (7): 3584-3588.
Roosenberg et al., "Studies and Syntheses of Siderophores, Microbial Iron Chelators, and Analogs as Potential Drug Delivery Agents," Current Medicinal Chemistry (2000) 7:159-197.
Wittmann et al., "New Synthetic Siderophores and Their β-Lactam Conjugates Based on Diamino Acids and Dipeptides," Bioorg. Med. Chem. (2002) 10: 1659-1670.
Cheng, Ji et al. Iron Transport-Mediated Drug Delivery: Practical Syntheses and In-Vitro Antibacterial Studies of Tris-Catecholate Siderophore-Aminopenicillin Conjugates Reveals Selectively Potent Antipseudomonal Activity. Journal of the American Chemical Society, Jun. 4, 2012, vol. 134 No. 24 pp. 9898-9901.
Martell, Arthur E. et al. "Development of Iron Chelators for Cooley's Anemia", Inorganica Chimica Acta., 1987, vol. 138. pp. 215-230.
Feb. 27, 2014, Semkina, A., "International Search Report", PCT/US2013/066408.
Oct. 20, 2015, Bai, Lingfei, "International Preliminary Report on Patentability", PCT/US2013/066408.
Jan. 13, 2014, Semkina, A. "Written Opinion of the International Search Authority" PCT/2013/066408.

*Primary Examiner* — Yong Chong
(74) *Attorney, Agent, or Firm* — Neifeld IP Law, PC

(57) ABSTRACT

An artificial tris-catecolate siderophore with a tripodal backbone and its conjugates with ampicillin and amoxicillin were synthesized. Both conjugates exhibited significantly enhanced in vitro antibacterial activities against Gram-negative species compared to the parent drugs, especially against *P. aeruginosa*. The conjugates appear to be assimilated by an induced bacterial iron transport process as their activities were inversely related to iron concentration. The easily synthesized tris-catecolate siderophores can be used with a variety of drugs as conjugates to target antibiotic-resistant Gram-negative bacteria.

9 Claims, 2 Drawing Sheets

ANTI-BACTERIAL SIDEROPHORE-AMINOPENICILLIN CONJUGATES

RELATED APPLICATIONS

This application claims priority under 35 U.S.C. §119(e) to U.S. Provisional Patent Application No. 61/687,101, filed Apr. 18, 2012, which is incorporated herein by reference.

GOVERNMENT SUPPORT

This invention was made with government support under contract numbers AI054193 and T32 GM075762 awarded by the National Institutes of Health. The United States Government has certain rights in the invention.

BACKGROUND OF THE INVENTION

The development of antimicrobial resistance among Gram-negative pathogens poses a serious threat to global public health. Among several mechanisms of antibiotic resistance in Gram-negative bacteria, a major problem is the low permeability of their outer membranes that serve as barriers to prevent antibiotic uptake by passive diffusion. Thus, the development of methods to overcome this permeability-mediated resistance is an important therapeutic goal.

During the course of infection, most microbes assimilate physiologically essential iron by synthesizing and utilizing high affinity ferric ion chelators, called siderophores. The Fe(III)-siderophore complexes are recognized and active transport through the bacterial cell membrane is initiated via specific receptors. Attachment of antibiotics to siderophores produces potential "Trojan Horse" conjugates that may enter pathogenic bacteria via their iron uptake system, thereby circumventing the permeability-mediated drug resistance problem. While studies of both natural and artificial siderophore-drug conjugates (sideromycins) have demonstrated their potential for development of antimicrobial agents, additional studies are needed to develop sufficiently selective active agents. New siderophore mimics that have selective antibiotic activity are thus needed in the art.

*Pseudomonas aeruginosa* is an opportunistic Gram-negative bacterium that endangers immunocompromised patients, including those with cystic fibrosis (CF), cancer, or AIDS. Once the infection is established it is very difficult to eradicate because *P. aeruginosa* is intrinsically resistant to many of existing antibiotics, including β-lactams. Inadequate penetration through the cell envelope is a significant factor in the resistance of *P. aeruginosa* to β-lactam antibiotics such as ampicillin and amoxicillin.

Like many other types of bacteria, strains of *P. aeruginosa* have developed receptors to recognize and transport Fe(III)-siderophore complexes from other species (xenosiderophores) in order to gain a competitive growth advantage. Enterobactin is a tris-catecholate siderophore primarily found in Gram-negative bacteria, such as *Escherichia coli* and *Salmonella typhimurium*. Enterobactin can also promote iron uptake into *P. aeruginosa* and the uptake is specifically inducible by enterobactin under iron-limiting conditions. Using enterobactin as a shuttle to deliver antibiotics into *P. aeruginosa* and other producing bacteria is an attractive strategy to pursue. However, this approach would be synthetically challenging because enterobactin has no functionality or site suitable for drug conjugation. Thus, new siderophore conjugates are needed to advance the study of antibiotic selectivity and to provide antibiotics effective against drug-resistant bacteria.

SUMMARY

The invention provides synthetic conjugates of a relatively simple siderophore mimic and various antibiotics. The conjugates can demonstrate selectively potent anti-bacterial activity, including anti-pseudomonal activity, while the parent antibiotics, themselves, are inactive. The invention this provides iron transport-mediated drug delivery systems comprising the compounds described herein. The compound can include a tris-catecholate siderophore with a tripodal backbone and as a conjugate with an antibiotic such as ampicillin or amoxicillin.

Conjugates evaluated as described herein exhibited significantly enhanced antibacterial activities against Gram-negative species compared to the parent drugs, especially against *P. aeruginosa*. The conjugates can be assimilated by an induced bacterial iron transport process and their activities are typically inversely related to iron concentration. The easily synthesized tris-catecholate siderophores can be used to prepare various drug conjugates to target antibiotic-resistant Gram-negative bacteria.

Accordingly, the invention provides a compound of Formula (I):

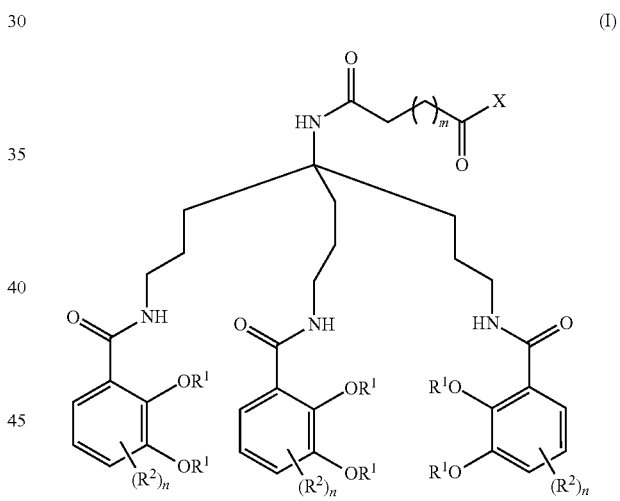

wherein
X is an antibiotic covalently linked to the illustrated structure of Formula (I) via an ester or amide bond;
m is 0 or 1-11;
each $R^1$ is independently H, —C(=O)alkyl, —C(=O)aryl, or —C(=O)O-alkyl;
each $R^2$ is independently H, alkyl, alkoxy, hydroxy, carboxy, halo, nitro, amino, or cyano; and
each n is independently 1, 2, or 3;
or a pharmaceutically acceptable salt or solvate thereof.

In one embodiment, each $R^1$ is a ($C_1$-$C_6$)alkanoyl group. In one embodiment, each $R^1$ is acetyl, propanoyl, or benzoyl. In one specific embodiment, each $R^1$ is acetyl. In another specific embodiment, each $R^1$ is H.

In one embodiment, each $R^2$ is H, alkyl, alkoxy, or hydroxy. In one specific embodiment, each $R^2$ is H. $R^2$ can also be a substituent as described below for the definition of substituents.

In some embodiments, each R¹ is the same, while in other embodiments, R¹ groups can be different. Likewise, in various embodiments, each R² can be the same, while in other embodiments, R² groups can be different from each other, for example, depending on the starting material selected to prepare the compounds.

In one embodiment, each n is 1. In other embodiments, n can be independently 1, 2 or 3; or 1 or 2; or 2 or 3. In some embodiments, m can be 0, 1, 2, 3, 4, 5, 6, 7, 8, 9, 10, 11, or a range from any one of the aforementioned integers to any other of the aforementioned integers. In various embodiments, m is 0, 1, 2, or 3. In some embodiments, the carbon of the parentheses marked by the letter m and its adjacent methylene can be replaced by a linker as defined below.

The variable X can be, for example, amikacin, amoxicillin, ampicillin, amphotericin, bacillomycin, cefalotin, chloramphenicol, chlortetracycline, ciprofloxacin, clindamycin, clindamycin phosphate, cycloserince, daptomycin, demeclocycline, doxorubicin, doxycycline, erythromycin, ethambutol, erythromycin, gentamicin, isoniazid, kanamycin, lincomycin, loracarbef, methacycline, mupirocin, neomycin, nystatin, oxytetracycline, pyrrolnitrin, rifampin, rolitetracycline, streptomycin, sulfacetamide, sulfabenzamide, sulfadiazine, sulfadoxine, sulfamerazine, sulfamethazine, sulfamethizole, sulfamethoxazole, sulfisoxazole, or tetracycline. In certain specific embodiments, X is ampicillin or amoxicillin.

In certain specific embodiments, the compound of Formula (I) is

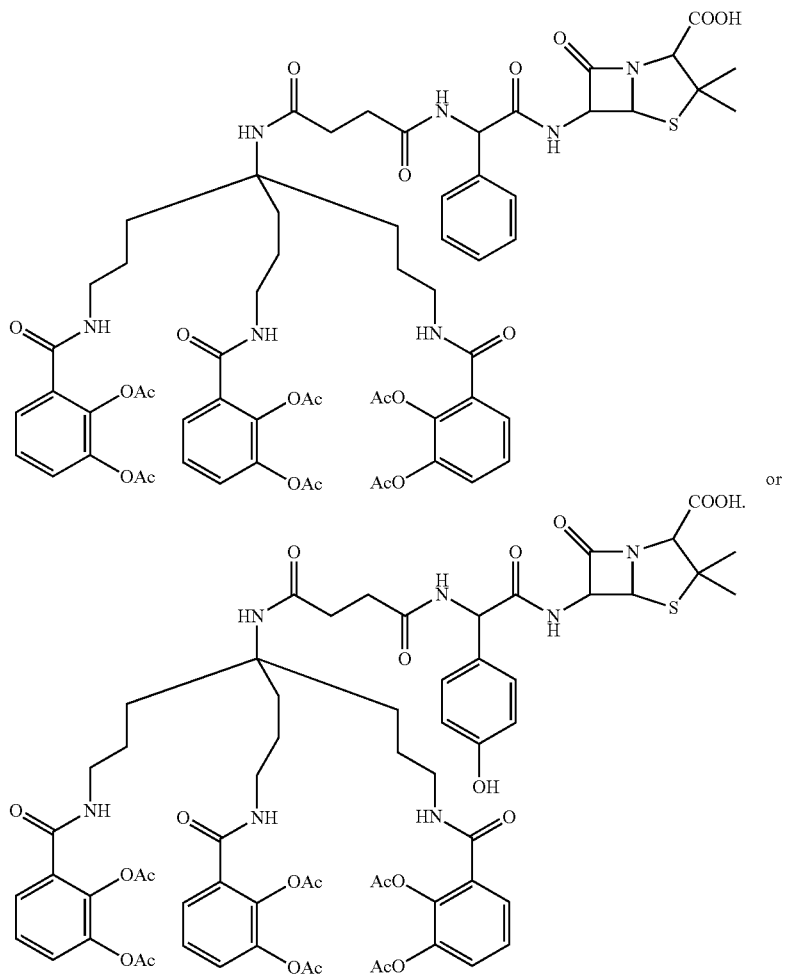

The invention also provides compositions of the compounds of Formula (I), for example, a compound of Formula (I) in combination with a pharmaceutically acceptable diluent, excipient, or carrier.

The invention further provides methods of treating a Gram-negative bacterial infection. The methods can include administering to a subject in need thereof an effective therapeutic amount of a compound described herein, thereby treating the bacterial infection. The invention yet further provides methods of killing or inhibiting the growth of a Gram-negative bacterium where the methods include contacting the bacterium with an effective lethal or inhibitory amount of a compound described herein. The bacterial infection can be caused by an antibiotic-resistant bacterium. In some embodiments, the bacterial infection is caused by a Pseudomonal bacterium. In some specific embodiments, the bacterial infection can be caused by *Pseudomonas aeruginosa, Escherichia coli, Acinetobacter baumannii*, or *Salmonella typhimurium.*

The invention also provides a method of increasing the permeability of a Gram-negative bacterium cell membrane to an antibiotic comprising conjugating an antibiotic to a compound of Formula (A) to provide a compound of Formula (I), and administering the compound to the bacterium cell membrane, thereby increasing the permeability of the Gram-negative bacterium cell membrane to the antibiotic as a result of its conjugation to the siderophore.

The invention additionally provides novel compounds of the formula described herein, intermediates for the synthesis of the compounds, as well as methods of preparing the compounds. The invention also provides compounds of the formulas described herein that are useful as intermediates for the synthesis of other useful compounds.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DETAILED DESCRIPTION

The invention provides iron transport-mediated drug delivery compounds and methods. The synthesis and efficacy of the compounds have been evaluated and selective anti-pseudomonal compounds have been discovered. The invention provides various synthetic conjugates of a relatively simple siderophore mimic and antibiotics, which conjugates have selectively potent anti-bacterial activity, while the parent antibiotics, themselves, are less active or substantially completely inactive.

Figure 1:
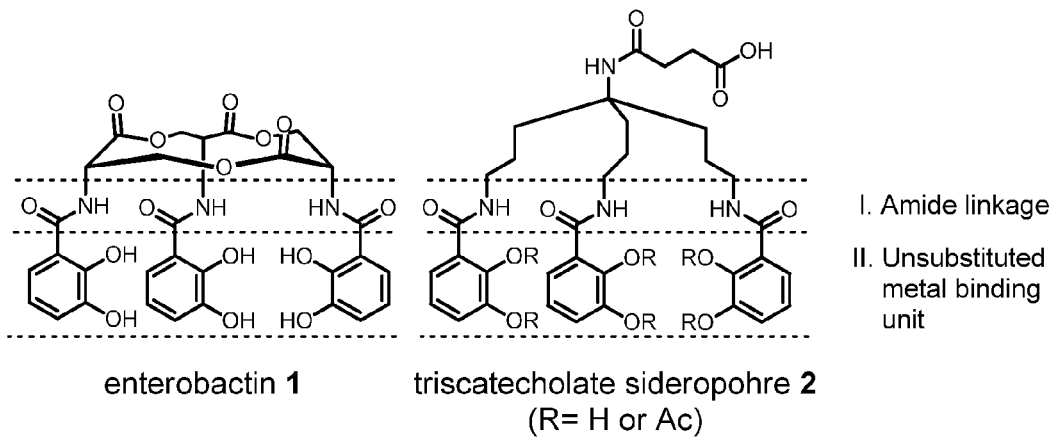
FIG. 1. Structures of enterobactin 1 and triscatecholate siderophore 2.
Figure 1:
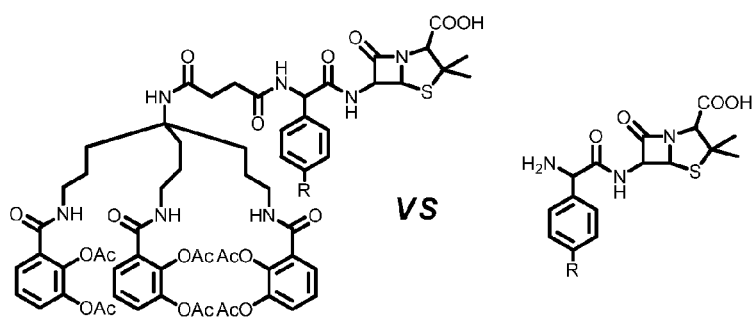

Investigation of receptor binding and transport of Fe(III)-enterobactin has revealed that an unsubstituted triscatechol iron center and the coordinated catechol amide groups are essential for recognition as a siderophore. To develop practical syntheses of microbe-selective sideromycins, simplified symmetrical siderophore analogs like 2 (FIG. 1) with linkers remote from the site of iron binding were developed as suitable scaffolds for conjugation to antibiotics.

The syntheses of triscatecholate siderophore 9 and its aminopenicillin conjugates (10 and 11) are summarized in Scheme 1. As the backbone of the artificial siderophore, tricarbamate 4 was synthesized from trinitrile 3 according to a published procedure (Unciti-Broceta et al., *J. Med. Chem.* 2008, 51, 4076) with minor modifications.

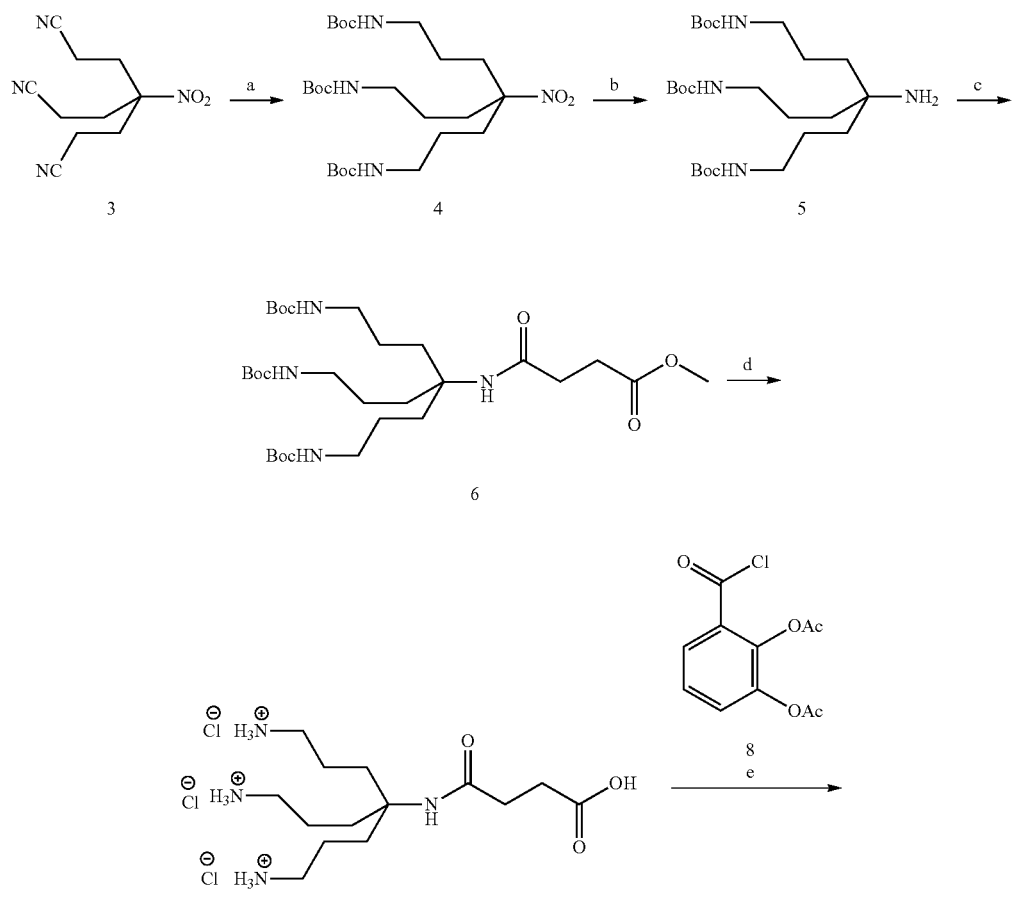

Scheme 1. Syntheses of the tris-catecholate siderophore and conjugates 10 and 11.

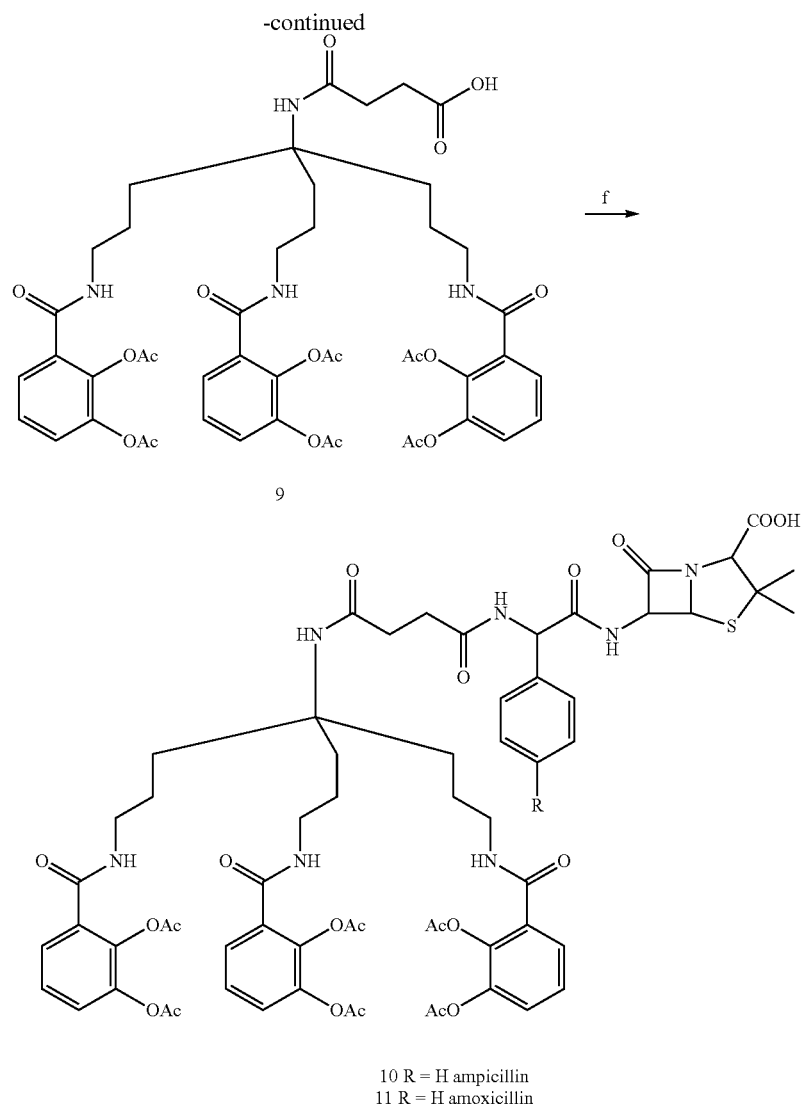

10 R = H ampicillin
11 R = H amoxicillin

Reagents and conditions: (a) 1. BH₃-THF, THF, reflux; 2. Boc₂O, Et₃N, MeOH, reflux, 83% for 2 steps; (b) NiCl₂, NaBH₄, MeOH, sonication, rt, 92%; (c) Methyl succinyl chloride, Et₃N, CH₂Cl₂, 0° C. to rt, 75%; (d) 6 N HCl, reflux, 100%; (e) 2,3-Diacyloxybenzoyl chloride 8, aqueous NaHCO₃/THF, 0° C. to rt, 57%; (f) 1. Isobutyl chloroformate, N-methyl morpholine, THF, 0° C.; 2. ampicillin or amoxicillin, Et₃N, THF/H₂O, 0° C. to rt, 55% (for 10), 50% (for 11).

In brief, trinitrile 3 was reduced with borane in THF and the resulting triamine was protected with Boc₂O to give tricarbamate 4. Reduction of the nitro group in 4 was accomplished with NaBH₄ in the presence of a catalytic amount of NiCl₂ to give amine 5 in 92% yield. Treatment of amine 5 with methyl succinyl chloride provided a succinate derivative 6, of which the carboxyl terminus later served as the coupling site with the aminopenicillins.

Treatment of 6 with 6 N HCl effected simultaneous removal of the Boc protecting groups and hydrolysis of the methyl ester to give triamino acid 7 as its tris HCl salt in quantitative yield. Using acylated catecholates as the siderophore components has the benefit of not only facilitating synthesis but also preventing pharmacological side effects of the catechol groups. The acylated catecholates can serve as prodrugs to the required iron binding catechols while circumventing potential methylation by a catechol O-methyltransferase (COMT) that would lead to a permanent loss of effective iron binding ability necessary for siderophore activity. Therefore, triamino acid 7 was acylated with 2,3-diacyloxybenzoyl chloride 8 in aqueous sodium bicarbonate to give tripodal siderophore 9, which can serve as a common intermediate for attachment of various amino or hydroxyl-containing drugs via an amide or ester linkage. Various analogs of compound 9 can be prepares, such as compounds of Formula (A), to serve as an analogous intermediate for conjugation to antibiotics.

As a proof-of-principle study, two aminopencillins, ampicillin and amoxicillin, which by themselves are not active against wild type strains of *P. aeruginosa*, were chosen for the syntheses of conjugates. Thus, siderophore 9 was coupled via its mixed anhydride with ampicillin and amoxicillin to provide conjugates 10 and 11, respectively. Conjugates 10 and 11 were first evaluated for their antibacterial ability against a collection of strains of *P. aeruginosa* using the agar well diffusion test. The influence of iron concentration on antibacterial activity was probed as well by conducting assays in iron-rich and iron-deficient media.

As shown in Table 1, the parent drugs, ampicillin and amoxicillin, were inactive or only weakly active against wild type strains of *P. aeruginosa* (KW799/wt, PAO1, Pa4, and Pa6) due to low membrane permeability. This was confirmed by studies of inhibition of the *P. aeruginosa* permeable mutant K799/61 in the assay, where both drugs are highly active as indicated by the large zones of inhibition they induced. Thus, strains of *P. aeruginosa* have the target of these classical antibiotics, but they cannot normally be accessed by passive diffusion.

iron-restricted conditions. Interestingly, both conjugates 10 and 11 showed no activity against a clinical isolate *P. aeruginosa* Pa6 even under iron-deficient conditions, potentially because Pa6 as well as PAO1 and Pa4 are different from each other in the type of pyoverdins they produce and utilize.

A further investigation of dependence of antibacterial activity on siderophore receptors was conducted with wild type *E. coli* H1443 and mutant H1876, which has defects in its

TABLE 1

Diameter of growth inhibition zones (mm) in the agar diffusion antibacterial susceptibility assay.

|  | 10$^a$ | | 11 | | Ampicillin | | Amoxicillin | |
| --- | --- | --- | --- | --- | --- | --- | --- | --- |
|  | +Fe | −Fe | +Fe | −Fe | +Fe | −Fe | +Fe | −Fe |
| *P. aeruginosa* KW799/wt | 20 | 24 | 25 | 26 |  | 23p | 27 | 18p |
| *P. aeruginosa* KW799/61 | 13P | 21 | 13P | 26 | 40 | 40 | 42 | 39 |
| *P. aeruginosa* PAO1 | 0 | 16 | 0 | 19 | 0 | 0 | 0 | 0 |
| *P. aeruginosa* Pa4 | 0 | 18 | 0 | 20 | 0 | h | 0 | h |
| *P. aeruginosa* Pa6 | 0 | 0 | 0 | 0 | 0 | 0 | 0 | 0 |
| *P. aeruginosa* K648 (pvd−, pch−) | 0 | 15 | 0 | 17 | 0 | 0 | 0 | 0 |
| *E. coli* H1443 (fepA+, cir+, fiu+) | 0 | 19 | 0 | 21 | 19/23P | 16/23p | 19/24P | 19/23p |
| *E. coli* H1876 (fepA−, cir−, fiu−) | 0 | 0 | 0 | 14p | 0 | 0 | 0 | 0 | p, partially clear inhibition zone/colonies in the inhibition zone;
P, unclear inhibition zone/many colonies in the inhibition zone;
h: indicates only a hint of growth inhibition detectable;
Exactly 50 μL of a 0.2 mM solution of each compound dissolved in 1:9 DMSO/MeOH was added to 9 mm wells in agar media (Standard I Nutrient Agar, Serva or Mueller Hinton II Agar, Becton, Dickinson and Company);
Inhibition zones were read after incubation at 37° C. for 24 hours.
$^a$Compound 10 was tested at 0.1 mM.

Addition of the siderophore portion to ampicillin or amoxicillin significantly increased their antibiotic activity against wild type *P. aeruginosa* strains except Pa6, especially in iron-deficient media, which reflects the situation in vivo in the infected host. As two control samples, siderophore 9 and its conjugate with phenylglycinamide (an analog of 10 without the β-lactam fragment, see Examples below) did not show any inhibitory effect in the agar well diffusion test, clearly indicating that the observed activity of the conjugates 10 and 11 was totally due to the β-lactam warhead.

The expression of genes that encode siderophore transport systems is induced in bacteria by low iron availability, but repressed when iron is sufficient. Therefore, the augmented activities of conjugates 10 and 11 represent the increased expression of appropriate siderophore receptors at the pathogen cell surface under iron limited conditions. This was demonstrated in assays with *P. aeruginosa* K648, a strain deficient for its native siderophore pyoverdin and pyochelin biosynthesis. While both conjugates 10 and 11 were inactive against the K648 strain in the iron-rich medium, the activities were largely elevated when tested in the iron-deficient medium, indicating that uptake of the conjugates was induced under iron-restricted conditions.

enterobactin-mediated iron transport system (Table 1). Compared to the wild type strain H1443, the activities of both conjugates drastically decreased against the triple mutant H1876 (fepA−, cir−, fiu−, genes that encode the receptors of Fe(III)-enterobactin and its hydrolysis products in *E. coli*), clearly indicating that the conjugates use the enterobactin-mediated iron transport system to penetrate the bacterial outer membrane barrier.

Conjugates 10 and 11 were subjected to further assays to determine their minimum inhibitory concentrations (MIC in μM) in both iron-rich and iron-deficient media (Table 2). Both conjugates exhibited excellent antibacterial activity against the various wild type strains of *P. aeruginosa* in iron-deficient medium, with MICs ranging from 0.05 to 0.39 μM, while ampicillin and amoxicillin were generally inactive (>100 μM). The only exception was Pa6, against which both conjugates were inactive, consistent with the observation from the agar diffusion assay. In iron-rich media, the inhibitory activities of the conjugates were largely impaired, further demonstrating that iron concentration of the media regulates the expression of siderophore outer membrane receptors and is thus inversely related to the activity of siderophore-drug conjugates.

TABLE 2

In Vitro antibacterial activities of siderophore-β-lactam conjugates 10 and 11 (MIC).

|  | 10 | | 11 | | Ampicillin | | Amoxicillin | |
| --- | --- | --- | --- | --- | --- | --- | --- | --- |
|  | +Fe | −Fe | +Fe | −Fe | +Fe | −Fe | +Fe | −Fe |
| *P. aeruginosa* KW799/wt | 33 | 0.05 | 25 | 0.05 | >200 | >200 | >200 | >200 |
| *P. aeruginosa* KW799/61 | 12.5 | 0.067 | 12.5 | 0.083 | 0.52 | 0.78 | 0.46 | 0.39 |
| *P. aeruginosa* PAO1 | 50 | 0.39 | 50 | 0.39 | >200 | >100 | >200 | >100 |
| *P. aeruginosa* Pa4 | 25 | 0.39 | 25 | 0.21 | >200 | >100 | >200 | >100 |
| *P. aeruginosa* Pa6 | >200 | >200 | >200 | >200 | >200 | >200 | >200 | >200 |
| *E. coli* ATCC 25922 | 150 | 1.56 | 100 | 6.25 | 16.7 | 12.5 | 4.17 | 4.17 |
| *K. pneumoniae* ATCC 8303 X68 | >200 | >100 | >200 | >100 | >200 | >100 | 100 | >100 |

$^a$MIC$_{90}$ values (µM) were determined using the broth microdilution method in Mueller-Hinton broth No. 2 (MHII) with visual end point analysis according to the CLSI guidelines (*Methods for Dilution Antimicrobial Susceptibility Tests for Bacteria that Grow Aerobically*, 8th ed. (Villanova, Pa., USA), Clinical and Laboratory Standards Institute (CLSI), 2009, approved standard document M07-A7).
$^b$Each compound was tested in triplicate.

Conjugates 10 and 11 were also tested against selected strains of *E. coli* and *Klebsiella pneumoniae*, both of which are able to synthesize and utilize enterobactin and its degraded product for iron uptake under iron-limited conditions. When tested against *E. coli*, conjugate 10 showed an 8-fold increase relative to ampicillin while conjugate 11 was almost as equipotent as amoxicillin. In sharp contrast to the activity enhancement observed in *P. aeruginosa* strains, both conjugates were found to be inactive (>100 µM) against *K. pneumoniae*. It appears that *P. aeruginosa*, *E. coli* and *K. pneumoniae*, either induced or inherently, have different abilities to use triscatecholate 2 as a siderophore for iron uptake. Another possibility for the high MICs from *K. pneumoniae* is that resistant mutants could develop and proliferate in the time course of the assay. Similar phenomena were observed in studies of *E. coli* exposed to catechol-based siderophore-loracarbef conjugates (Ghosh et al., *Chem. Biol.* 1996, 3, 1011) and *P. aeruginosa* exposed to pyoverdin-ampicillin conjugates (Kinzel et al., *J. Antibiot.* 1998, 51, 499). Isolation of mutants and studies of bacterial growth kinetics in the presence of the conjugates are currently under investigation.

In summary, artificial tris-catecholate siderophores with tripodal backbones and their conjugates with ampicillin and amoxicillin were synthesized and studied. Relative to the parent drugs, both conjugates exhibited significantly enhanced antibacterial activities against Gram-negative species, especially against *P. aeruginosa*. The conjugates use energy dependent active bacterial iron uptake systems to bypass the Gram-negative outer membrane permeability barrier, which accounts for their increased activities. The easily synthesized tris-catecholate siderophores can be used as new drug conjugates that have different cellular targets and modes of action against Gram-negative bacteria.

DEFINITIONS

As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with the recitation of claim elements or use of a "negative" limitation.

The term "and/or" means any one of the items, any combination of the items, or all of the items with which this term is associated. The phrase "one or more" is readily understood by one of skill in the art, particularly when read in context of its usage. For example, one or more substituents on a phenyl ring refers to one to five, or one to four, for example if the phenyl ring is disubstituted.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values, e.g., weight percents, proximate to the recited range that are equivalent in terms of the functionality of the individual ingredient, the composition, or the embodiment.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to treat a disease, disorder, and/or condition, or to bring about a recited effect. For example, an effective amount can be an amount effective to reduce the progression or severity of the condition or symptoms being treated. Determination of a therapeutically effective amount is well within the capacity of persons skilled in the art. The term "effective amount" is intended to include an amount of a compound described herein, or an amount of a combination of compounds described herein, e.g., that is effective to treat or prevent a disease or disorder, or to treat the symptoms of the disease or disorder, in a host. Thus, an "effective amount" generally means an amount that provides the desired effect.

The terms "treating", "treat" and "treatment" include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" can extend to prophylaxis and can include prevent, prevention, preventing, lowering, stopping or reversing the progression or severity of the condition or symptoms being treated. As such, the term "treatment" can include medical, therapeutic, and/or prophylactic administration, as appropriate.

The terms "inhibit", "inhibiting", and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting.

Specific values listed below for radicals, substituents, and ranges, are for illustration only; they do not exclude other defined values or other values within defined ranges for radicals and substituents. Generic terms include each of their species. For example, the term halo includes and can explicitly be fluoro, chloro, bromo, or iodo.

The term "alkyl" refers to a branched, unbranched, or cyclic hydrocarbon having, for example, from 1-20 carbon atoms, and often 1-12, 1-10, 1-8, 1-6, or 1-4 carbon atoms. Examples include, but are not limited to, methyl, ethyl, 1-propyl, 2-propyl(iso-propyl), 1-butyl, 2-methyl-1-propyl(isobutyl), 2-butyl(sec-butyl), 2-methyl-2-propyl(t-butyl), 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, hexyl, octyl, decyl, dodecyl, and the like. The alkyl can be unsubstituted or optionally substituted, for example, with a substituent described below. The alkyl can also be optionally partially or fully unsaturated. As such, the recitation of an alkyl group can optionally include both alkenyl or alkynyl groups, in certain embodiments. The alkyl can be a monovalent hydrocarbon radical, as described and exemplified above, or it can be a divalent hydrocarbon radical (i.e., an alkylene), depending on the context of its use.

The term "alkoxy" refers to the group alkyl-O—, where alkyl is as defined herein. Examples of alkoxy groups include, but are not limited to, methoxy, ethoxy, n-propoxy, iso-propoxy, n-butoxy, tert-butoxy, sec-butoxy, n-pentoxy, n-hexoxy, 1,2-dimethylbutoxy, and the like. The alkoxy can be unsubstituted or substituted.

The term "aryl" refers to an aromatic hydrocarbon group derived from the removal of at least one hydrogen atom from a single carbon atom of a parent aromatic ring system. The radical attachment site can be at a saturated or unsaturated carbon atom of the parent ring system. The aryl group can have from 6 to 20 carbon atoms, for example, about 6-10 carbon atoms, in the cyclic skeleton. The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or optionally substituted, as described for alkyl groups.

A "linker" or "linking group" refers to an organic or inorganic chain or moiety that connects to other groups of a molecule. A linker can be, for example, a group L where L is a an alkylene, an alkenylene, an aryl diradical, a direct bond or a divalent radical of the formula —W—Z—W—; where each W is independently —N(R')C(=O)—, —C(=O)N(R')—, —OC(=O)—, —C(=O)O—, —O—, —S—, —S(O)—, —S(O)$_2$—, —N(R')—, —C(=O)—, —(CH$_2$)$_n$— where n is 1-3, —(CX*$_2$)—, —(CH$_2$)$_n$—(CX*$_2$)— where n is 1-3, or a direct bond; and Z is a divalent moiety selected from (C$_1$-C$_{12}$)alkyl, (C$_2$-C$_{12}$)alkenyl, (C$_2$-C$_{12}$)alkynyl, (C$_3$-C$_8$)cycloalkyl, (C$_6$-C$_{10}$)aryl, —N(R')C(=O)—, —C(=O)N(R')—, —OC(=O)—, —C(=O)O—, —N(R')—, —C(=O)—, —(CX*$_2$)—, —(CH$_2$)$_n$—(CX*$_2$)$_n$— where n is 1-3, —(OCH$_2$—CH$_2$)$_n$— where n is 1 to about 10, —C(O)NH(CH$_2$)$_n$— where n is 1 to about 6, —OP(O)(OH)O—, —OP(O)(OH)O(CH$_2$)$_n$— where n is 1 to about 6, —OP(O)(OH)OCH$_2$CH(OH)CH$_2$—, —N$^+$(Me)$_2$(CH$_2$)$_n$— where n is 1 to about 6; or (C$_1$-C$_{12}$)alkyl, (C$_2$-C$_{12}$)alkenyl, (C$_2$-C$_{12}$)alkynyl, or —(OCH$_2$—CH$_2$)$_n$-optionally interrupted between two carbons, or between a carbon and an oxygen, with a (C$_3$-C$_8$) cycloalkyl, heteroaryl, heterocycle, or (C$_6$-C$_{10}$)aryl group, where n is 1 to about 6; or Z is a direct bond.

The term "substituted" indicates that one or more (e.g., 1, 2, 3, 4, or 5; in some embodiments 1, 2, or 3; and in other embodiments 1 or 2) hydrogen atoms on the group indicated in the expression using "substituted" is replaced with a "substituent". The substituent can be one of a selection of the indicated group(s), or it can be a suitable group known to those of skill in the art, provided that the substituted atom's normal valency is not exceeded, and that the substitution results in a stable compound. Suitable substituent groups include, e.g., alkyl, alkenyl, alkynyl, alkoxy, halo, haloalkyl, hydroxy, hydroxyalkyl, aryl, aroyl, heteroaryl, heterocycle, cycloalkyl, alkanoyl, alkoxycarbonyl, amino, alkylamino, dialkylamino, trifluoromethylthio, difluoromethyl, acylamino, nitro, trifluoromethyl, trifluoromethoxy, carboxy, carboxyalkyl, keto, thioxo, alkylthio, alkylsulfinyl, alkylsulfonyl, arylsulfinyl, arylsulfonyl, heteroarylsulfinyl, heteroarylsulfonyl, heterocyclesulfinyl, heterocyclesulfonyl, phosphate, sulfate, hydroxylamine, hydroxyl (alkyl)amine, and cyano, as well as the moieties illustrated in the schemes and Figures of this disclosure, and combinations thereof. Additionally, suitable substituent groups can be, e.g., —X, —R, —O⁻, —OR, —SR, —NR₂, —NR₃, =NR, —CX₃, —CN, —OCN, —SCN, —N=C=O, —NCS, —NO, —NO₂, =N₂, —N₃, NC(=O)R, —C(=O)R, —C(=O)NRR, —S(=O)₂O⁻, —S(=O)₂OH, —S(=O)₂R, —OS(=O)₂OR, —S(=O)₂NHR, —S(=O)R, —OP(=O)(OR)₂, —P(=O)(OR)₂, —OP(=O)(OH)(OR), —P(=O)(OH)(OR), —P(=O)(O⁻)₂, —P(=O)(OH)₂, —C(=O)R, —C(=O)X, —C(S)R, —C(O)OR, —C(O)O⁻, —C(S)OR, —C(O)SR, —C(S)SR, —C(O)NRR, —C(=S)NRR, —C(=NR)NRR, where each X is independently a halogen ("halo"): F, Cl, Br, or I; and each R is independently H, alkyl, aryl, (aryl)alkyl (e.g., benzyl), heteroaryl, (heteroaryl)alkyl, heterocycle, heterocycle(alkyl), or a protecting group. As would be readily understood by one skilled in the art, when a substituent is keto (=O) or thioxo (=S), or the like, then two hydrogen atoms on the substituted atom are replaced. In some embodiments, one or more of the substituents above are excluded from the group of potential values for substituents on the substituted group.

The term "solvate" refers to a solid compound that has one or more solvent molecules associated with its solid structure. Solvates can form when a solid compound is crystallized from a solvent, wherein one or more solvent molecules become an integral part of the solid crystalline matrix. The compounds of the formulas described herein can be solvates, for example, ethanol solvates. Another type of a solvate is a hydrate. A "hydrate" likewise refers to a solid compound that has one or more water molecules intimately associated with its solid or crystalline structure at the molecular level. A hydrate is a specific type of a solvate. Hydrates can form when a compound is solidified or crystallized in water, wherein one or more water molecules become an integral part of the solid crystalline matrix. The compounds of the formulas described herein can be hydrates.

An antibiotic is an agent that inhibits bacterial or fungal growth or kills bacteria or fungi. Antibiotics can be linked to the structure of Formula (I) via an amide or other linking group. Accordingly, any antibiotic that has an available hydroxyl or amino group can be linked to the structure of Formula (A), either by direct condensation of an amine and the a carboxy group of Formula (A), such as in compound 9, or by first carrying out a functional group transformation of a hydroxyl of the antibiotic to an amine, followed by amide formation with Formula (A). Antibiotics that can be linked to Formula (A) to provide a compound of Formula (I) include, but are not limited to, antibiotics of the lincomycin family (a class of antibiotic agents originally recovered from *streptomyces lincolnensis*); antibiotics of the tetracycline family (a class of antibiotic agents originally recovered from *streptomyces aureofaciens*); and sulfur-based antibiotics such as the sulfonamides. A wide variety of antibiotics can be conjugated to Formula (A), such as the antibacterials described at http://en.wikipedia.org/wiki/Antibacterial. Some specific useful examples include the following.

Beta-lactams that can be conjugated include penems, carbapenems (imipenem, meropenem, ertapeneme, doripenem, panipenem, biapenem, and the like), monobactams (aztreonam, tigimonam, carumonam, BAL30072, and the like), as well as a variety of other beta-lactam cell envelope antibiotics (see: http://en.wikipedia.org/wiki/Monobactam).

Specific examples of some suitable antibiotics of the lincomycin family include lincomycin, clindamycin, and clindamycin phosphate.

Specific examples of macrolide antibiotics include erythromycin, azithromycin, clarithromycin, dirithromycin, roxithromycin, telithromycin, carbomycin A, josamycin, kitasamycin, midecamycin/midecamycin acetate, oleandomycin, solithromycin, spiramycin, troleandomycin, and tylosin/tylocine.

Specific examples of ketolide antibiotics include telithromycin, cethromycin, solithromycin, spiramycin, ansamycin, oleandomycin, carbomycin, and tylosin.

Specific examples of antibiotics of the tetracycline family include tetracycline itself, chlortetracycline, oxytetracycline, demeclocycline, rolitetracycline, methacycline and doxycycline.

Specific examples of sulfur-based antibiotics include the sulfonamides sulfacetamide, sulfabenzamide, sulfadiazine, sulfadoxine, sulfamerazine, sulfamethazine, sulfamethizole, sulfisoxazole, and sulfamethoxazole.

Further examples of linkable antibiotics include the oxazolidinones such as zyvox (linezolid), peptide antibiotics such as the polymixins, quinolones, fluoroquinolones (http://en.wikipedia.org/wiki/Quinolone), aminoglycosides (http://en.wikipedia.org/wiki/Aminoglycoside), and rifamycins (http://en.wikipedia.org/wiki/Rifamycin).

Linkable antibiotics can also include various antibacterial agents, antifungal agents, antimycotic agents and antiviral agents; penicillins such as ampicillin or amoxicillin, cephalosporins such as cephalothin and ceclor (cephachlor), aminoglycosides such as, kanamycin, macrolides such as erythromycin, nystatin, and amphotericin; and the antibiotics amikacin, bacillomycin, chloramphenicol, doxorubicin, doxycycline, ethambutol, erythromycin, gentamicin, isoniazid, kanamycin, carbacephalosporins such as lorabid (loracarbef), mupirocin, neomycin, pyrrolnitrin, rifampin, streptomycin, and vancomycin.

General Synthetic Methods

Preparation of the compounds described herein can be prepared according to the methods in the Examples below, or may be prepared according to known techniques in the art of organic synthesis. Many linking groups for conjugating antibiotics to Formula (I) are commercially available, and/or can be prepared as described in the art. Information regarding general synthetic methods that may be used to prepare the compounds described herein, particularly with respect employing linking groups, may be found in Greg T. Hermanson, *Bioconjugate Techniques*, Academic Press, San Diego, Calif. (1996). Useful linkers and conjugation techniques that can be used to link antibiotics to Formula (A) are further described by Roosenberg et al., *Curr. Med. Chem.* 2000, 7, 159; Wittmann et al., *Bioorg. Med. Chem.* 2002, 10, 1659; and Heinisch et al., *J. Med. Chem.* 2002, 45, 3032. Additional useful reactions well known to those of skill in the art are referenced in *March's Advanced Organic Chemistry Reactions, Mechanisms, and Structure*, $5^{th}$ Ed. by Michael B. Smith and Jerry March, John Wiley & Sons, Publishers; and Wuts et al. (1999), *Protective Groups in Organic Synthesis*, $3^{rd}$ Ed., John Wiley & Sons, Publishers.

The methods of preparing compounds of the invention can produce isomers in certain instances. Although the methods of the invention do not always require separation of these isomers, such separation may be accomplished, if desired, by methods known in the art. For example, preparative high performance liquid chromatography methods may be used for isomer purification, for example, by using a column with a chiral packing.

Compounds of Formula (I) can be readily prepared by condensing an antibiotic having an available hydroxy or amine group, or a carboxy after reduction to an alcohol, with a compound of Formula (A):

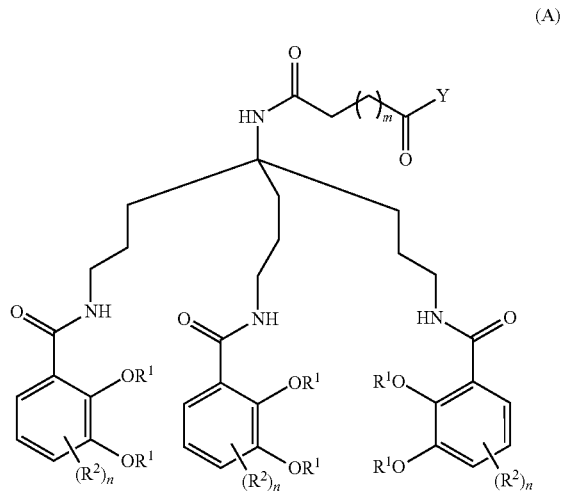

(A)

wherein Y is a leaving group such as a halogen (e.g., to couple with an amine or alcohol), for example, chloride. The moiety —C(=O)Y of Formula (A) can also be an activated carbonyl or active ester, and the remaining variables are as described for Formula (I). Such condensations can be carried out in the presence of a suitable solvent and a base (e.g., triethylamine or the like), often advantageously at or below room temperature. If the antibiotic does not have an available amine moiety but has a hydroxyl available for forming a linkage with Formula (A), the hydroxyl group of the antibiotic can be directly coupled to form an ester or first esterified with a group such as an alkanoic acid having an terminal (optionally protected) amino group, for example, 2-aminoacetic acid or 3-aminopropionic acid, followed by a condensation reaction described above, to provide a compound of the invention.

Pharmaceutical Formulations

The compounds described herein can be used to prepare therapeutic pharmaceutical compositions, for example, by combining the compounds with a pharmaceutically acceptable diluent, excipient, or carrier. The compounds may be added to a carrier in the form of a salt or solvate. For example, in cases where compounds are sufficiently basic or acidic to form stable nontoxic acid or base salts, administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartrate, succinate, benzoate, ascorbate, α-ketoglutarate, and β-glycerophosphate. Suitable inorganic salts may also be formed, including hydrochloride, halide, sulfate, nitrate, bicarbonate, and carbonate salts.

Pharmaceutically acceptable salts may be obtained using standard procedures well known in the art, for example by reacting a sufficiently basic compound such as an amine with a suitable acid to provide a physiologically acceptable ionic compound. Alkali metal (for example, sodium, potassium or lithium) or alkaline earth metal (for example, calcium) salts of carboxylic acids can also be prepared by analogous methods.

The compounds of the formulas described herein can be formulated as pharmaceutical compositions and administered to a mammalian host, such as a human patient, in a variety of forms. The forms can be specifically adapted to a chosen route of administration, e.g., oral or parenteral administration, by intravenous, intramuscular, topical or subcutaneous routes.

The compounds described herein may be systemically administered in combination with a pharmaceutically acceptable vehicle, such as an inert diluent or an assimilable edible carrier. For oral administration, compounds can be enclosed in hard or soft shell gelatin capsules, compressed into tablets, or incorporated directly into the food of a patient's diet. Compounds may also be combined with one or more excipients and used in the form of ingestible tablets, buccal tablets, troches, capsules, elixirs, suspensions, syrups, wafers, and the like. Such compositions and preparations typically contain at least 0.1% of active compound. The percentage of the compositions and preparations can vary and may conveniently be from about 0.5% to about 60%, about 1% to about 25%, or about 2% to about 10%, of the weight of a given unit dosage form. The amount of active compound in such therapeutically useful compositions can be such that an effective dosage level can be obtained.

The tablets, troches, pills, capsules, and the like may also contain one or more of the following: binders such as gum tragacanth, acacia, corn starch or gelatin; excipients such as dicalcium phosphate; a disintegrating agent such as corn starch, potato starch, alginic acid and the like; and a lubricant such as magnesium stearate. A sweetening agent such as sucrose, fructose, lactose or aspartame; or a flavoring agent such as peppermint, oil of wintergreen, or cherry flavoring, may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propyl parabens as preservatives, a dye and flavoring such as cherry or orange flavor. Any material used in preparing any unit dosage form should be pharmaceutically acceptable and substantially non-toxic in the amounts employed. In addition, the active compound may be incorporated into sustained-release preparations and devices.

The active compound may be administered intravenously or intraperitoneally by infusion or injection. Solutions of the active compound or its salts can be prepared in water, optionally mixed with a nontoxic surfactant. Dispersions can be prepared in glycerol, liquid polyethylene glycols, triacetin, or mixtures thereof, or in a pharmaceutically acceptable oil. Under ordinary conditions of storage and use, preparations may contain a preservative to prevent the growth of microorganisms.

Pharmaceutical dosage forms suitable for injection or infusion can include sterile aqueous solutions, dispersions, or sterile powders comprising the active ingredient adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions, or by the use of surfactants. The prevention of the action of microorganisms can be brought about by various antibacterial and/or antifungal agents, for example, parabens, chlorobutanol, phenol, sorbic acid, thimerosal, and the like.

In many cases, it will be preferable to include isotonic agents, for example, sugars, buffers, or sodium chloride. Prolonged absorption of the injectable compositions can be brought about by agents delaying absorption, for example, aluminum monostearate and/or gelatin.

Sterile injectable solutions can be prepared by incorporating the active compound in the required amount in the appropriate solvent with various other ingredients enumerated above, as required, optionally followed by filter sterilization. In the case of sterile powders for the preparation of sterile injectable solutions, methods of preparation can include vacuum drying and freeze drying techniques, which yield a powder of the active ingredient plus any additional desired ingredient present in the solution.

For topical administration, compounds may be applied in pure form, e.g., when they are liquids. However, it will generally be desirable to administer the active agent to the skin as a composition or formulation, for example, in combination with a dermatologically acceptable carrier, which may be a solid, a liquid, a gel, or the like.

Useful solid carriers include finely divided solids such as talc, clay, microcrystalline cellulose, silica, alumina, and the like. Useful liquid carriers include water, dimethyl sulfoxide (DMSO), alcohols, glycols, or water-alcohol/glycol blends, in which a compound can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using a pump-type or aerosol sprayer.

Thickeners such as synthetic polymers, fatty acids, fatty acid salts and esters, fatty alcohols, modified celluloses, or modified mineral materials can also be employed with liquid carriers to form spreadable pastes, gels, ointments, soaps, and the like, for application directly to the skin of the user.

Examples of dermatological compositions for delivering active agents to the skin are known to the art; for example, see U.S. Pat. No. 4,992,478 (Geria), U.S. Pat. No. 4,820,508 (Wortzman), U.S. Pat. No. 4,608,392 (Jacquet et al.), and U.S. Pat. No. 4,559,157 (Smith et al.). Such dermatological compositions can be used in combinations with the compounds described herein where an ingredient of such compositions can optionally be replaced by a compound described herein, or a compound described herein can be added to the composition Useful dosages of the compounds described herein can be determined by comparing their in vitro activity, and in vivo activity in animal models. Methods for the extrapolation of effective dosages in mice, and other animals, to humans are known to the art; for example, see U.S. Pat. No. 4,938,949 (Borch et al.). The amount of a compound, or an active salt or derivative thereof, required for use in treatment will vary not only with the particular compound or salt selected but also with the route of administration, the nature of the condition being treated, and the age and condition of the patient, and will be ultimately at the discretion of an attendant physician or clinician.

The compound can be conveniently administered in a unit dosage form, for example, containing 5 to 1000 mg/m$^2$, conveniently 10 to 750 mg/m$^2$, most conveniently, 50 to 500 mg/m$^2$ of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The invention provides therapeutic methods of treating infections in a mammal, which involve administering to a mammal having an infection an effective amount of a compound or composition described herein. A mammal includes a primate, human, rodent, canine, feline, bovine, ovine, equine, swine, caprine, bovine and the like. The infection can be a bacterial infection, for example, one caused by a bacterium described herein.

The ability of a compound of the invention to treat a bacterial infection may be determined by using assays well known to the art. For example, the design of treatment protocols, toxicity evaluation, data analysis, quantification of cell kill, and the biological significance of the use of antibacterial screens are known. In addition, ability of a compound to treat a bacterial infection or kill or inhibit bacteria may be determined using the assays as described in the Examples below.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1

Compound Preparation

General Information. All reactions were carried out under argon by using standard techniques. All solvents and reagents were obtained from commercial sources and used without further purification unless otherwise stated. Tetrahydrofuran (THF) was distilled from sodium and benzophenone. Reactions were monitored by thin-layer chromatography (TLC) on 0.25 mm silica gel plates visualized under UV light, iodine or KMnO$_4$ staining. Silica gel column chromatography was performed using Sorbent Technologies silica gel 60 (32-63 μm). Reverse Phase C18 Silica Gel was a generous gift from Eli Lilly and Co. NMR spectra were recorded on a Varian 600 MHz spectrometer at ambient temperature. The HPLC analyses were carried out using YMC Pro C18 reverse phase column (3.0×50 mm). Mobile phases used were 10 mM ammonium acetate in HPLC grade water (A) and HPLC grade acetonitrile (B). A gradient was formed from 5%-80% of B in 10 min, then 80%-95% of B in 2 min, and then 95%-5% of B in 3 min at a flow rate of 0.7 mL/min (total run time of 15 min). Preparative HPLC purifications were performed on a Waters preparative binary pump system at a flow rate of 15 mL/min with a UV detector (254 nm) and a YMC-Pack Pro C18 column (150×20 mm, particle size 5 μm). A solvent gradient was formed from 10 mM aqueous ammonium acetate and acetonitrile with a flow rate of 15 mL/min.

Figure 2:
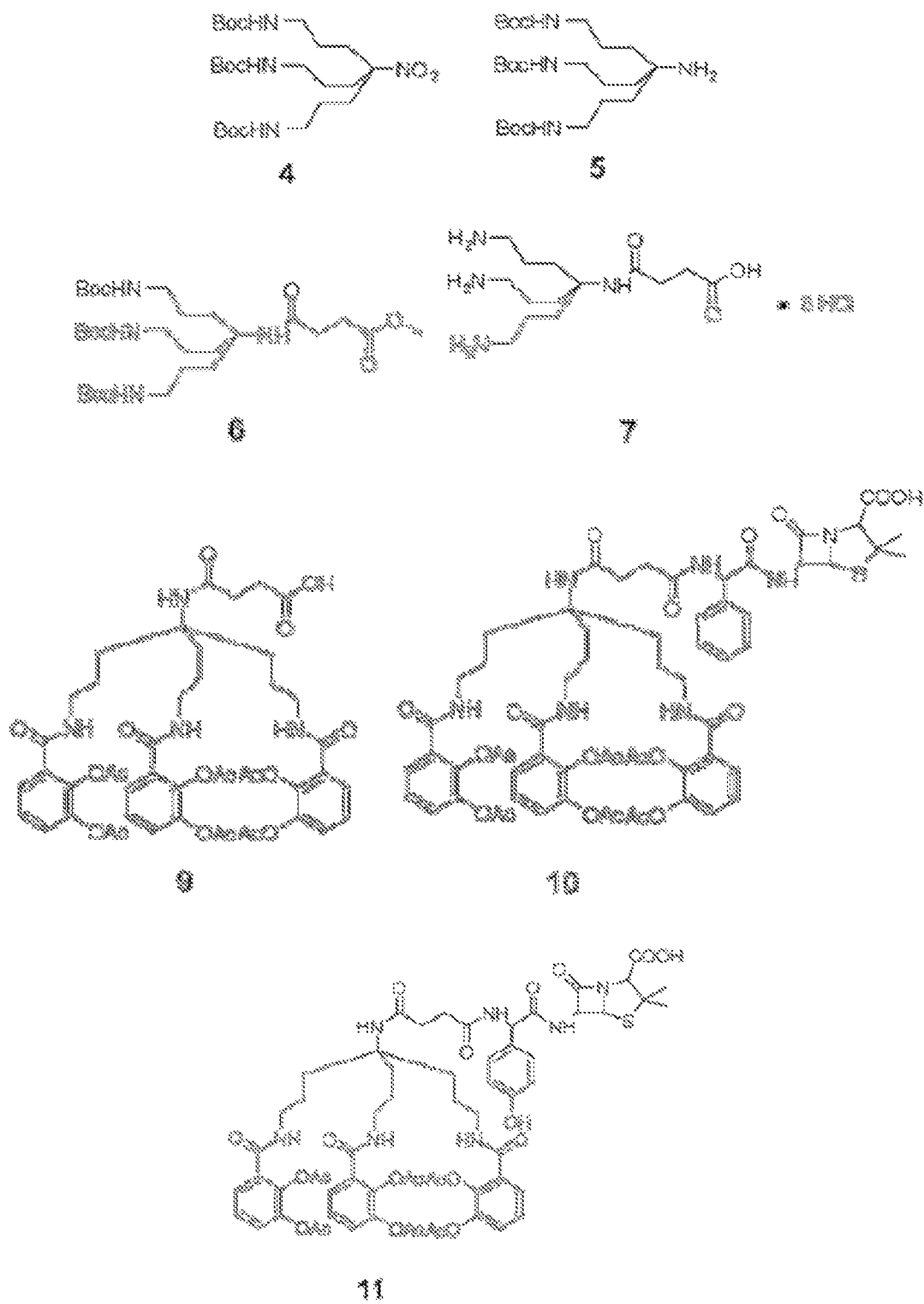
FIG. 2. Examples of intermediates and compounds of the invention, according to various embodiments.

The following compounds were prepared according to published procedures: trinitrile 3 (Newkome et al., *J. Org. Chem.*, 1988, 53, 5552-5554), methyl succinyl chloride (Cason, *J. Org. Synth.*, 1945, 25, 19), and 2,3-diacetoxybenzoic acid (Bergeron et al., *J. Org. Chem.*, 1980, 45, 1589-1592). The structures of compounds 4-10 are illustrated in FIG. 2.

Nitro Tricarbamate 4

This compound was prepared by a modified two step literature procedure (Unciti-Broceta et al., *J. Med. Chem.*, 2008, 51, 4076-4084). To a suspension of trinitrile 3 (3.30 g, 15.0 mmol) in 10 mL of anhydrous THF was added BH$_3$-THF complex (1.0 M in THF, 75 mL, 75.0 mmol). The solution was heated to reflux for 16 h. After cooling to room temperature (~22° C.), conc. HCl was added to destroy the excess borane and the mixture was heated with steam bath for 30 min. All solvent was removed under vacuum and the residue was basified with 40% NaOH solution (20 mL) and extracted with CH$_2$Cl$_2$ (100 mL×3). The combined organic layers were dried over Na$_2$SO$_4$ and filtered. The solvent was evaporated to give the crude amine which was dissolved in 40 mL of MeOH. To this solution were added Et$_3$N (8.4 mL, 60.0 mmol) and Boc$_2$O (10.8 g, 49.5 mmol) and the mixture was heated to reflux for 6 h. After removal of the solvent under vacuum, the residue was dissolved in 200 mL of EtOAc and the organic layer was washed sequentially with 0.5 N HCl, brine, dried over Na$_2$SO$_4$ and filtered. The solvent was removed under vacuum and the residue was purified by chromatography on a silica gel column (hexanes:EtOAc=3:1 to 1:1) to give compound 4 (6.63 g, 83% for 2 steps) as a colorless oil: $^1$H NMR (600 MHz, CDCl$_3$) δ4.86 (br. s., 3H), 3.00-3.05 (m, 6H), 1.75-1.89 (m, 6H), 1.23-1.42 (m, 33H); $^{13}$C NMR (150 MHz, CDCl$_3$) δ156.1, 93.9, 79.2, 40.2, 32.7, 28.4, 24.3.

Amino Tricarbamate 5

In an ultrasonic bath, NiCl$_2$-6H$_2$O (67 mg, 0.25 mmol) was dissolved in 3 mL of MeOH. NaBH$_4$ (29 mg, 0.75 mmol) was added in one portion and the resulting black suspension was sonicated for 30 min. To the above suspension was added compound 4 (250 mg, 0.5 mmol) dissolved in 3 mL of MeOH and NaBH$_4$ (57 mg, 1.5 mmol) sequentially. The mixture was sonicated for 30 min before additional NaBH$_4$ (57 mg, 1.5 mmol) was added. After 30 min, the mixture was filtered through a short pad of Celite and the solvent was evaporated. The residue was partitioned between 10 mL of water and 20 mL of CH$_2$Cl$_2$. The aqueous layer was extracted with CH$_2$Cl$_2$ (10 mL×3) and the combined organic layers were washed with brine, dried over Na$_2$SO$_4$ and filtered. The solvent was evaporated under vacuum to give amine 5 (217 mg, 92%) as a white foam: $^1$H NMR (600 MHz, CDCl$_3$) δ4.66 (br. s., 3H), 3.07-3.12 (m, 6H), 1.35-1.52 (m, 33H), 1.25-1.35 (m, 6H); $^{13}$C NMR (150 MHz, CDCl$_3$) 156.2, 79.3, 53.0, 41.2, 37.3, 28.6, 24.4; HRMS (ESI) calcd. for C$_{25}$H$_{51}$N$_4$O$_6$ (M+H)$^+$: 503.3803, found 503.3815.

Methyl Succinate 6

To a solution of compound 5 (1.12 g, 2.23 mmol) and Et$_3$N (0.62 mL, 4.46 mmol) in 10 mL of CH$_2$Cl$_2$ cooled to 0° C. was added methyl succinyl chloride (0.52 mL, 4.23 mmol). The mixture was stirred for 1 h at 0° C. and 1 h at room temperature. The solvent was removed under vacuum and the residue was partitioned between 50 mL of EtOAc and 50 mL of water. The aqueous layer was extracted with EtOAc (50 mL×3) and the combined organic layers were washed sequentially with sat. NaHCO$_3$, brine, dried over Na$_2$SO$_4$ and filtered. After removal of the solvent under vacuum, the residue was purified by chromatography on a silica gel column (50-100% EtOAc in hexanes) to give compound 6 (1.03 g, 75%) as a white waxy solid: mp=140-142° C.; $^1$H NMR (600 MHz, CDCl$_3$) δ5.48 (br. s., 1H), 4.76 (br. s., 3H), 3.67 (s, 3H), 3.04-3.10 (m, 6H), 2.62 (t, J=6.75 Hz, 2H), 2.40 (t, J=6.75 Hz, 2H), 1.59-1.69 (m, 6H), 1.42 (s, 27H), 1.39 (br. s., 6H); $^{13}$C NMR (150 MHz, CDCl$_3$) δ173.9, 170.9, 156.3, 79.3, 58.6, 52.1, 40.8, 32.3, 31.8, 29.4, 28.6, 23.8; HRMS (ESI) calcd. for C$_{30}$H$_{57}$N$_4$O$_9$ (M+H)$^+$: 617.4120, found 617.4133.

Triamino Acid HCl Salt 7

A suspension of compound 6 (880 mg, 1.43 mmol) in 20 mL of 6 M HCl was heated to reflux for 30 min. After cooling to room temperature, all solvent was removed under vacuum. The oily residue was dissolved in 10 mL of water and freeze dried to give the HCl salt of triamino acid 7 in quantitative yield as a glassy solid: $^1$H NMR (600 MHz, D$_2$O) δ2.92 (t, J=7.48 Hz, 6H), 2.56 (t, J=6.75 Hz, 2H), 2.47 (t, J=6.75 Hz, 2H), 1.64-1.70 (m, 6H), 1.49-1.58 (m, 6H); $^{13}$C NMR (150 MHz, D$_2$O) δ177.0, 174.1, 58.0, 39.5, 30.8, 30.5, 28.9, 20.7; HRMS (ESI) calcd. for C$_{14}$H$_{31}$N$_4$O$_3$ (M+H)$^+$: 303.2391, found 303.2398.

2,3-Diacyloxybenzoyl chloride 8

To a suspension of 2,3-diacetoxybenzoic acid (2.38 g, 10 mmol) in 30 mL of CH$_2$Cl$_2$ were added oxalyl chloride (1.72 mL, 20 mmol) and anhydrous DMF (0.1 mL). The solution was stirred at room temperature for 1 h and all solvent was removed under vacuum to give crude acyl chloride 8 as a yellow semi-solid which was used immediately in the next step.

Triscatecolate Siderophore 9

To a solution of salt 7 (575 mg, 1.4 mmol) in 20 mL of 0.5 M NaHCO$_3$ cooled to 0° C. was added a solution of acyl chloride 8 (1.2 g, 4.69 mmol, assuming quantitative yield from the previous step) in 20 mL of THF in a rate of 1 mL/min using a syringe pump. After addition, the mixture was stirred for 1 h at 0° C. and 1 h at room temperature. After removal of the THF under vacuum, the aqueous solution was acidified to pH=2 with 3 M HCl and extracted with EtOAc (20 mL×3). The combined organic layers were washed with brine, dried over Na$_2$SO$_4$, filtered and concentrated under vacuum. The residue was purified by chromatography on a reverse-phase silica gel column (C$_{18}$, CH$_3$CN: H$_2$O=1:2 to 2:3). The fractions containing product was combined and lyophilized to give compound 9 (0.77 g, 57%) as a white solid: $^1$H NMR (600 MHz, CDCl$_3$) δ7.51 (dd, J=7.5, 1.9 Hz, 3H), 7.21-7.30 (m, 6H), 6.62 (t, J=5.6 Hz, 3H), 5.67 (s, 1H), 3.31-3.35 (m, 6H), 2.49-2.52 (m, 2H), 2.26-2.32 (m, 20H), 1.70-1.75 (m, 6H), 1.48-1.52 (m, 6H); $^{13}$C NMR (150 MHz, CDCl$_3$) δ174.9, 171.9, 168.8, 168.6, 165.8, 143.1, 140.3, 130.7, 126.8, 126.5, 125.8, 58.8, 40.1, 32.1, 31.6, 29.2, 23.3, 20.8, 20.8; HRMS (ESI) calcd. for C$_{47}$H$_{55}$N$_4$O$_{18}$ (M+H)$^+$: 963.3506, found 963.3533; HPLC retention time 5.03 min.

Ampicillin Conjugate 10

To a solution of acid 9 (22 mg, 0.023 mmol) and N-methyl morpholine (2.5 μL, 0.023 mmol) in 1 mL of anhydrous THF cooled to 0° C. was added isobutyl chloroformate (3.0 μL, 0.023 mmol) and the mixture was stirred for 1 hour at that temperature. A solution of ampicillin trihydrate (10.6 mg, 0.026 mmol) and Et$_3$N (10 μL) in 1 mL of THF/H$_2$O 4:1 was added and the mixture was stirred for 1 h at 0° C. and 1 h at room temperature. After removal of the THF under vacuum, the residue was dissolved in 5 mL of water and the solution was acidified to pH=2 with 1 N HCl. The resulting suspension was extracted with EtOAc (5 mL×3) and the combined organic layers were washed with brine, dried over Na$_2$SO$_4$ and filtered. The solvent was removed under vacuum and the residue was purified by preparative HPLC. The fractions containing product was combined and lyophilized to give conjugate 10 (16.4 mg, 55%) as a white solid: $^1$H NMR (600 MHz, DMSO-$d_6$) δ9.06 (d, J=7.6 Hz, 1H), 8.54 (d, J=8.5 Hz, 1H), 8.31 (t, J=5.6 Hz, 3H), 7.40-7.44 (m, 5H), 7.24-7.36 (m, 9H), 7.12 (s, 1H), 5.71 (d, J=8.2 Hz, 1H), 5.46 (dd, J=7.9, 4.1 Hz, 1H), 5.35 (d, J=4.1 Hz, 1H), 4.11 (s, 1H), 3.12-3.16 (m, 6H), 2.43-2.45 (m, 2H), 2.30-2.34 (m, 2H), 2.27 (s, 9H), 2.20 (s, 9H), 1.59-1.65 (m, 6H), 1.53 (s, 3H), 1.37-1.43 (m, 9H); HRMS (ESI) calcd. for $C_{63}H_{72}N_7O_{21}S$ (M+H)$^+$: 1294.4496, found 1294.4522; HPLC retention time 5.57 min.

Amoxicillin Conjugate 11

Amoxicillin conjugate 11 was prepared and purified in a similar way to that of conjugate 10 from amoxicillin (15.2 mg, 50%): $^1$H NMR (600 MHz, DMSO-$d_6$) δ8.86 (d, J=7.9 Hz, 1H), 8.38 (d, J=8.2 Hz, 1H), 8.31 (t, J=5.6 Hz, 3H), 7.42-7.44 (m, 3H), 7.31-7.36 (m, 6H), 7.18 (d, J=8.5 Hz, 2H), 7.12 (s, 1H), 6.68 (d, J=8.5 Hz, 2H), 5.55 (d, J=8.2 Hz, 1H), 5.44 (dd, J=8.1, 4.0 Hz, 1H), 5.33 (d, J=3.8 Hz, 1H), 4.07 (s, 1H), 3.10-3.16 (m, 6H), 2.38-2.42 (m, 2H), 2.29-2.33 (m, 2H), 2.27 (s, 9H), 2.20 (s, 9H), 1.60-1.64 (m, 6H), 1.53 (s, 3H), 1.37-1.43 (m, 9H); HRMS (ESI) calcd. for $C_{63}H_{71}N_7NaO_{22}S$ (M+Na)$^+$: 1332.4265, found 1332.4279; HPLC retention time 5.30 min.

Phenylglycinamide Conjugate S1

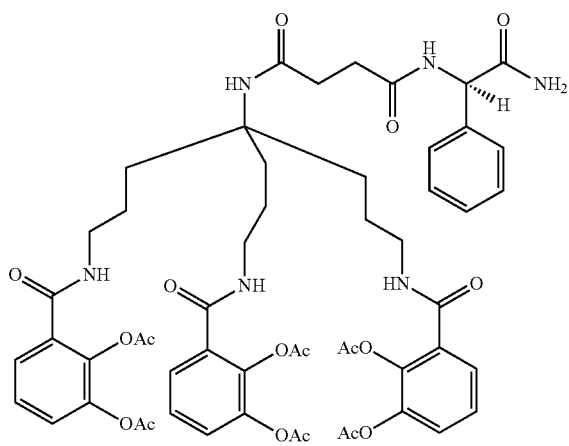

S1

To a solution of acid 9 (38 mg, 0.039 mmol) and N-methyl morpholine (4.5 μL, 0.041 mmol) in 1.5 mL of anhydrous THF cooled to 0° C. was added isobutyl chloroformate (5.2 μL, 0.040 mmol) and the mixture was stirred for 1 hour at that temperature. A solution of D-phenylglycinamide (8.6 mg, 0.057 mmol) and Et$_3$N (10 μL) in 1 mL of THF/H$_2$O 4:1 was added and the mixture was stirred for 1 h at 0° C. and 1 h at room temperature. After removal of the THF under vacuum, the residue was suspended in H$_2$O (5 mL) and extracted with EtOAc (5 mL×3). The combined organic layers were dried over Na$_2$SO$_4$ and filtered. The solvent was removed under vacuum and the residue was purified by chromatography on a silica gel column (5-8% MeOH in CH$_2$Cl$_2$) to give conjugate S1 (28 mg, 66%) as a white solid: $^1$H NMR (600 MHz, DMSO-$d_6$) δ8.41 (d, J=7.9 Hz, 1H), 8.31 (t, J=5.3 Hz, 3H), 7.65 (br. s., 1H), 7.25-7.45 (m, 14H), 7.13 and 7.12 (2×s, 2H), 5.36 (d, J=8.2 Hz, 1H), 3.11-3.17 (m, 6H), 2.35-2.48 (m, 2H), 2.30-2.34 (m, 2H), 2.28 (s, 9H), 2.21 (s, 9H), 1.58-1.67 (m, 6H), 1.37-1.44 (m, 6H); HRMS (ESI) calcd. for $C_{55}H_{63}N_6O_{18}$ (M+H)$^+$: 1095.4193, found 1095.4203.

Example 2

Antibiotic Assays

General Materials and Methods.

All liquids and media were sterilized by autoclaving (121° C., 15 min) before use. All aqueous solutions and media were prepared using distilled, deionized, and filtered water (Millipore Milli-Q Advantage A10 Water Purification System). Luria broth (LB) was purchased from VWR. Mueller-Hinton No. 2 broth (MHII broth; cation adjusted) was purchased from Sigma-Aldrich (St. Louis, Mo.). Iron-deficient (—Fe) MHII broth was prepared by adding 0.8 mL of a 1 mg/mL sterile aq. solution of 2,2'-bipyridine to 49.2 mL of MHII broth. Iron-rich (+Fe) MHII broth was prepared by adding 0.8 mL of a 1 mg/mL sterile aq. solution of FeCl$_3$ to 49.2 mL of MHII broth. Mueller-Hinton No. 2 agar (MHII agar; HiMedia Laboratories) was purchased from VWR. Iron-deficient (–Fe) MHII agar was prepared by adding 0.5 mL of a 1 mg/mL sterile aq. solution of 2,2'-bipyridine to 34 mL of melted MHII agar with gentle mixing. Iron-rich (+Fe) MHII agar was prepared by adding 0.5 mL of a 1 mg/mL sterile aq. solution of FeCl$_3$ to 34 mL of melted MHII agar with gentle mixing. See also Wencewicz, T. A. Dissertation, University of Notre Dame, Notre Dame, Ind., 2011, for relevant techniques.

Antibacterial Susceptibility Testing by the Agar Diffusion Assay.

Antibacterial activity of the compounds was determined by a modified Kirby-Bauer agar diffusion assay. Overnight cultures of test organisms were grown in LB broth for 18-24 h and standard suspensions of 1.5×10$^6$ CFU/mL were prepared in saline solution (0.9% NaCl) according to a 0.5 BaSO$_4$ McFarland Standard. This standardized suspension (0.1 mL) was added to 34 mL of sterile, melted agar (–Fe or +Fe) tempered to 47-50° C. After gentle mixing, the inoculated agar media was poured into a sterile plastic petri dish (145 mm×20 mm) and allowed to solidify near a flame with the lid ajar for about 30 min. Wells of 9.0 mm diameter were cut from the petri dish agar and filled with exactly 50 μL of the test sample solution. The petri dish was incubated at 37° C. for 18-24 h and the inhibition zone diameters were measured (mm) with an electronic caliper after 24 h.

Determination of MIC$_{90}$ Values by the Broth Microdilution Assay.

Antibacterial activity of the compounds was determined by measuring their minimum inhibitory concentrations (MIC$_{90}$'s) using the broth microdilution method according to the Clinical and Laboratory Standards Institute (CLSI, formerly the NCCLS) guidelines. Each well of a 96-well microtiter plate was filled with 50 μL of sterile broth media (–Fe or +Fe). Each test compound was dissolved in DMSO making a 20 mM solution, and then diluted with sterile broth media (–Fe or +Fe) to 400 or 800 μM. Exactly 50 μL of the compound solution was added to the first well of the microtiter plate and 2-fold serial dilutions were made down each row of the plate. Exactly 50 μL of bacterial inoculum (5×10$^5$ CFU/mL in broth media) was then added to each well giving a total volume of 100 μL/well. The plate was incubated at 37° C. for 20 h and then each well was examined for bacterial growth. The MIC$_{90}$ was recorded as the lowest compound concentration (μM) required to inhibit 90% of bacterial growth as judged by turbidity of the culture media relative to a row of wells filled with a DMSO standard.

Example 3

Pharmaceutical Dosage Forms

The following formulations illustrate representative pharmaceutical dosage forms that may be used for the therapeutic or prophylactic administration of a compound of a formula described herein, a compound specifically disclosed herein, or a pharmaceutically acceptable salt or solvate thereof (hereinafter referred to as 'Compound X'):

| (i) Tablet 1 | mg/tablet |
|---|---|
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| 'Compound X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| 'Compound X' | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/mL) | mg/mL |
|---|---|
| 'Compound X' (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/mL) | mg/mL |
|---|---|
| 'Compound X' (free acid form) | 10.0 |
| Monobasic sodium phosphate | 0.3 |
| Dibasic sodium phosphate | 1.1 |
| Polyethylene glycol 400 | 200.0 |
| 0.1N Sodium hydroxide solution (pH adjustment to 7.0-7.5) | q.s. |
| Water for injection | q.s. ad 1 mL |

| (vi) Aerosol | mg/can |
|---|---|
| 'Compound X' | 20 |
| Oleic acid | 10 |
| Trichloromonofluoromethane | 5,000 |
| Dichlorodifluoromethane | 10,000 |
| Dichlorotetrafluoroethane | 5,000 |

| (vii) Topical Gel 1 | wt. % |
|---|---|
| 'Compound X' | 5% |
| Carbomer 934 | 1.25% |
| Triethanolamine (pH adjustment to 5-7) | q.s. |
| Methyl paraben | 0.2% |
| Purified water | q.s. to 100 g |

| (viii) Topical Gel 2 | wt. % |
|---|---|
| 'Compound X' | 5% |
| Methylcellulose | 2% |
| Methyl paraben | 0.2% |
| Propyl paraben | 0.02% |
| Purified water | q.s. to 100 g |

| (ix) Topical Ointment | wt. % |
|---|---|
| 'Compound X' | 5% |
| Propylene glycol | 1% |
| Anhydrous ointment base | 40% |
| Polysorbate 80 | 2% |
| Methyl paraben | 0.2% |
| Purified water | q.s. to 100 g |

| (x) Topical Cream 1 | wt. % |
|---|---|
| 'Compound X' | 5% |
| White bees wax | 10% |
| Liquid paraffin | 30% |
| Benzyl alcohol | 5% |
| Purified water | q.s. to 100 g |

| (xi) Topical Cream 2 | wt. % |
|---|---|
| 'Compound X' | 5% |
| Stearic acid | 10% |
| Glyceryl monostearate | 3% |
| Polyoxyethylene stearyl ether | 3% |
| Sorbitol | 5% |
| Isopropyl palmitate | 2% |
| Methyl Paraben | 0.2% |
| Purified water | q.s. to 100 g |

These formulations may be prepared by conventional procedures well known in the pharmaceutical art. It will be appreciated that the above pharmaceutical compositions may be varied according to well-known pharmaceutical techniques to accommodate differing amounts and types of active ingredient 'Compound X'. Aerosol formulation (vi) may be used in conjunction with a standard, metered dose aerosol dispenser. Additionally, the specific ingredients and proportions are for illustrative purposes. Ingredients may be exchanged for suitable equivalents and proportions may be varied, according to the desired properties of the dosage form of interest.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A compound of Formula (I):

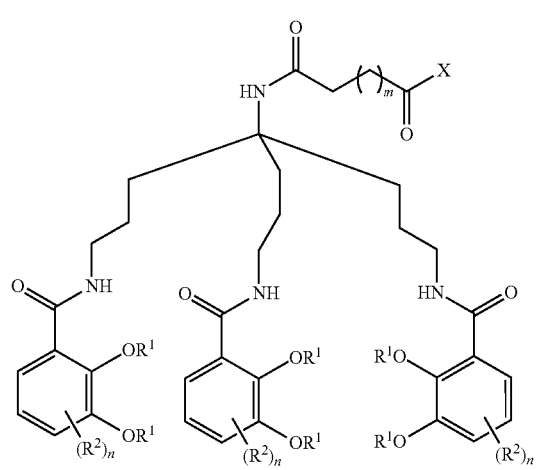

(I)

wherein m is 0 or 1-11;

each $R^1$ is independently H, —C(=O)alkyl, —C(=O)aryl, or —C(=O)O-alkyl;

each $R^2$ is independently H, alkyl, alkoxy, hydroxy, carboxy, halo, nitro, amino, or cyano;

each n is independently 1, 2, or 3; and

X is amikacin, amoxicillin, ampicillin, amphotericin, aztreonam, bacillomycin, BAL30072, biapenem, carumonam, cefaclor, cefalotin, chloramphenicol, chlortetracycline, ciprofloxacin, clindamycin, clindamycin phosphate, cycloserine, daptomycin, demeclocycline, doripenem, doxorubicin, doxycycline, ertapeneme, erythromycin, ethambutol, erythromycin, gentamicin, imipenem, isoniazid, kanamycin, lincomycin, loracarbef, meropenem, methacycline, mupirocin, neomycin, nystatin, oxytetracycline, panipenem, pyrrolnitrin, rifampin, rolitetracycline, streptomycin, sulfacetamide, sulfabenzamide, sulfadiazine, sulfadoxine, sulfamerazine, sulfamethazine, sulfamethizole, sulfamethoxazole, sulfisoxazole, tetracycline, or tigimonam, X being covalently linked via an ester or amide bond;

or a pharmaceutically acceptable salt or solvate thereof.

2. The compound of claim 1 wherein each $R^1$ is acetyl, propanoyl, or benzoyl.

3. The compound of claim 1 wherein each $R^2$ is H, alkyl, alkoxy, or hydroxy.

4. The compound of claim 1 wherein each $R^2$ is H.

5. The compound of claim 1 wherein each n is 1.

6. The compound of claim 1 wherein m is 0, 1, 2, or 3.

7. The compound of claim 1 wherein X is ampicillin or amoxicillin.

8. The compound of claim 1 wherein the compound is

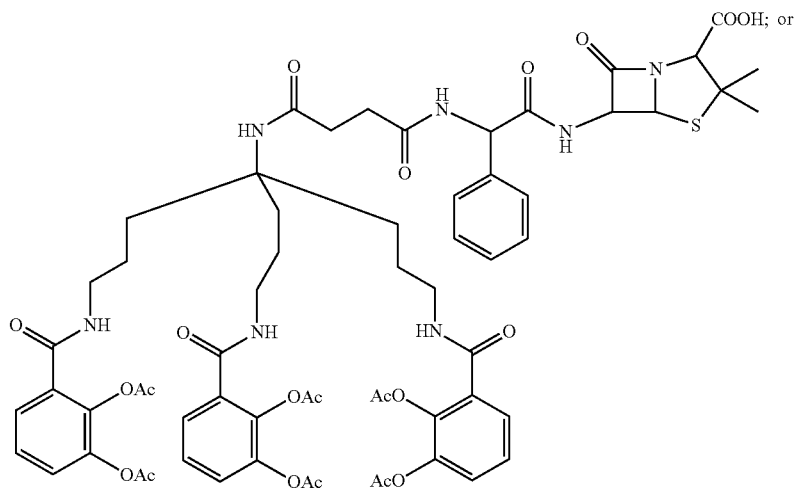

-continued
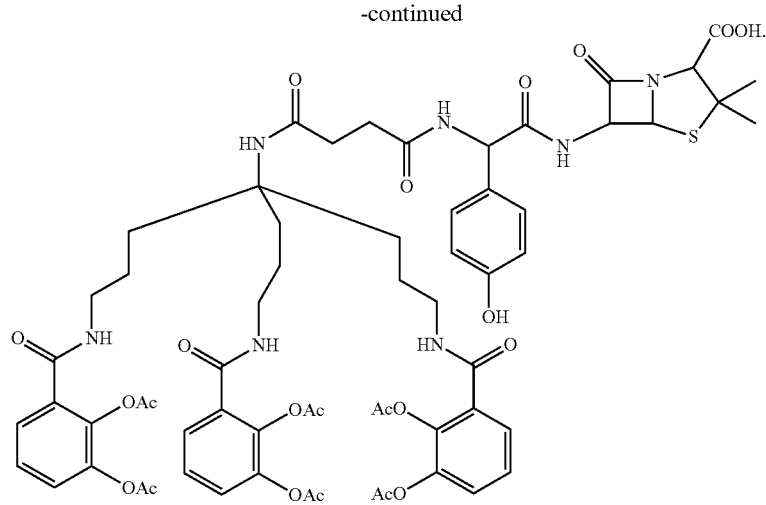
9. A composition comprising a compound of claim 1 and a pharmaceutically acceptable diluent or carrier.
* * * * *